United States Patent [19]

Arakaki

[11] Patent Number: 4,752,970

[45] Date of Patent: Jun. 28, 1988

[54] PROTECTIVE FACE SHIELD

[76] Inventor: Steven Y. Arakaki, 927 Laki Rd., Honolulu, Hi. 96817

[21] Appl. No.: 62,636

[22] Filed: Jun. 16, 1987

[51] Int. Cl.[4] ............................ F41H 1/04; A61F 9/00
[52] U.S. Cl. ................................. 2/2.5; 2/6; 2/9; 2/424; 89/36.17; 102/293; 428/911
[58] Field of Search .................... 2/2.5, 2, 6, 9, 424, 2/422, 410, 426; 89/36.17, 36.14, 36.05; 102/293; 428/911

[56] References Cited

U.S. PATENT DOCUMENTS 3,123,831 3/1964 Wells et al. ........................ 2/9 X
3,858,242 1/1975 Gooding ........................... 2/2.5 X
3,893,368 7/1975 Wales, Jr. ........................ 89/36.17
4,368,660 1/1983 Held ............................... 428/911 X
4,689,834 9/1987 McCarthy et al. .................. 2/6 X

FOREIGN PATENT DOCUMENTS 2368598 5/1978 France ............................. 89/36.17

Primary Examiner—Peter Nerbun
Attorney, Agent, or Firm—James Creighton Wray

[57] ABSTRACT

A ballistic face shield is provided for military use and acts to deflect penetrating bullets. Thickness is avoided by angling the orientation of the shield and by providing an explosive charge which launches the shield forwardly and upwardly when an outer layer of the shield is shattered. The shield construction includes glass, inert gas and plastic layers.

9 Claims, 2 Drawing Sheets

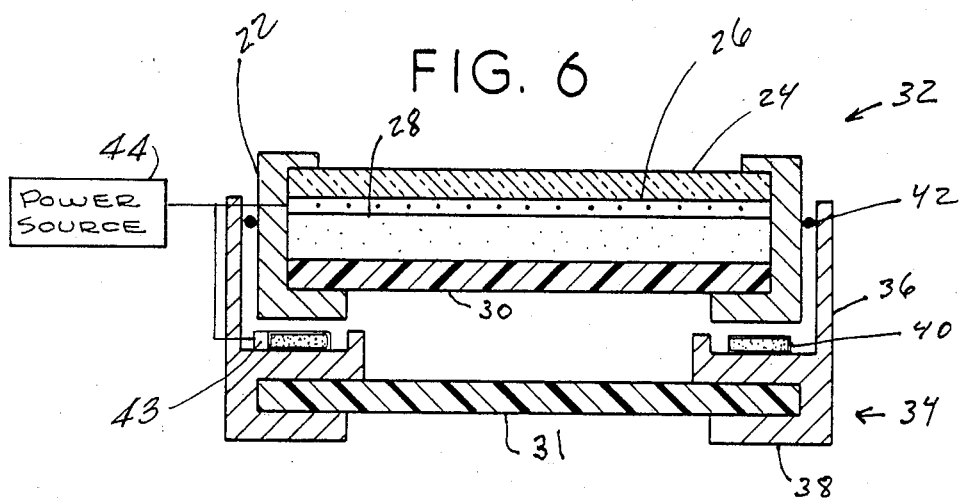
FIG. 6
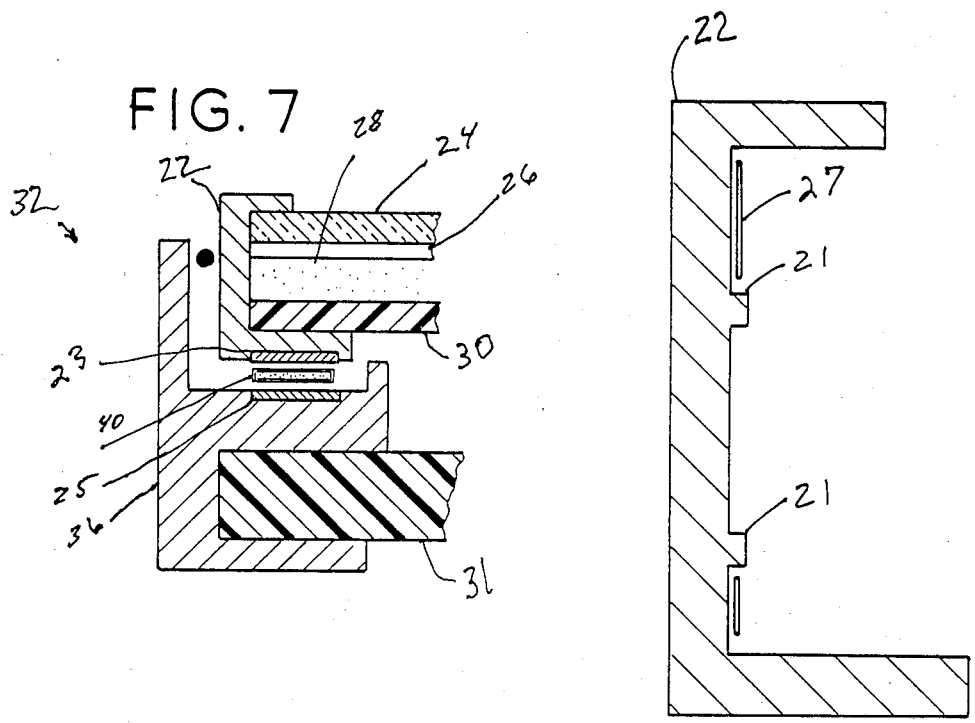
FIG. 7
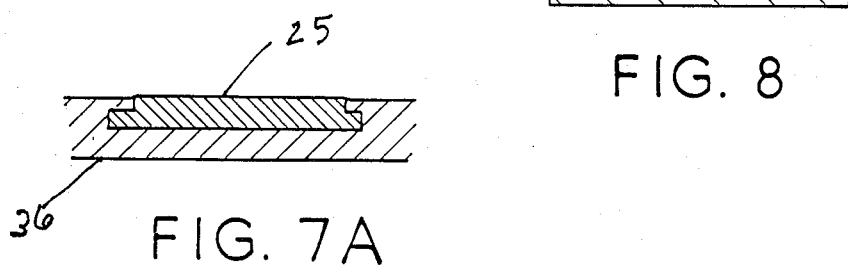
FIG. 7A
FIG. 8

PROTECTIVE FACE SHIELD

BACKGROUND OF THE INVENTION

The present invention relates to protective shields generally.

Protective shields have been used in the past as an attachment to helmets, such as motorcycle helmets.

Increasingly, military applications of face shields have been considered as an attachment to battle helmets as a means to reduce or eliminate projectile penetration of the facial area of soldiers.

Bulletproof shields have had success as plate glass replacements in commercial establishments. However, these bulletproof shields tend to be thick and cumbersome and unsuitable for any but planar shapes.

A satisfactory face shield which acts as an effective antiballistic has heretofore been unknown.

SUMMARY OF THE INVENTION

The present invention solves many of the problems associated with the prior art shields.

The invention includes a shield that attaches to a helmet. The shield is designed to provide better protection against projectiles in that, unlike other types of eye protective devices, the present invention is designed to provide protection against a bullet. The shield could be utilized by tank crews, infantry, or aircraft and helicopter crews. Other situations where eye protection is needed, such as motorcycle helmets, could also utilize the device.

The invention operates on the principle of deflection as opposed to absorption of impact. The difference is significant. Absorption of impact requires resistance to penetration which is achieved by thickening the material used. A relatively large amount of mass is necessary to absorb the impact of a bullet traveling in a straight line path. A substantially smaller amount of mass is required to deflect a bullet so that the path of the bullet is altered away from the user.

In order to accomplish the purpose of the invention, the present invention provides a shield that is slanted to provide an upwardly angled profile so that any projectile striking the face shield is naturally deflected upwardly.

The shield itself is fabricated in a multi-ply construction and is provided with an explosive charge which launches the shield in a forward and upward motion when the outer layer of the shield is shattered. The purpose for doing this is to allow the innermost layer of the shield to deflect the projectile upwardly away from the user's face.

As mentioned, the shield itself is preferably of multiply construction with the outer layer being tempered glass. Tempered glass has a high degree of toughness and fractures in a way suitable to the overall purpose of the invention which will be explained later.

The outer layer of tempered glass is also practical since it is scratch-resistant and easy to clean.

The next layer is a thin sheet of glass having crisscrossing copper wires embedded in the glass. The layer acts to trigger explosive charges which will be described in greater detail. The wires are severable such that, when the wires are severed by an incoming projectile, after fracturing of the glass, the explosive charges are detonated. The thickness of the wire should be as small as possible so that a tighter criss-crossing pattern can be achieved. Also, smaller wires tend to avoid vision obstruction. This layer of glass having criss-crossing copper wires embedded therein operates in the preferred embodiment but can be eliminated if other means of detecting the penetration of the tempered glass layer is used. Such other means include infrared light or strain measuring means.

The next layer is actually a gas layer of inert gas material. The gas layer is used to keep out moisture between the gas and the innermost layer. Otherwise, moisture could condense upon the glass when the temperature drops and obscure the vision of the user. The gas layer also provides the explosive charges time to ignite, and launch the innermost layer.

The innermost layer is preferably high impact resistant plastic, preferably polycarbonate plastic. This layer is principally responsible for deflecting the incoming projectile. The layer of plastic is propelled along with a stainless steel rim when the explosive charges are set off. The stainless steel rim tends to reinforce and rigidify the plastic layer.

The stainless steel rim also provides an extremely strong base upon which the explosive charge reacts to complete the launching of the shield.

The explosive charge is disposed between two sections of the stainless steel rim. The explosive is ignited from the bottom and allowed to propagate upwardly along the sides of the stainless steel rim sections to achieve a controlled burn. Propellants which have a lower burn rate can be substituted but only with modification to the burn pattern and design of the face shield.

A final innermost layer of plastic material completes the shield. This layer is provided with a rim, also made of stainless steel, which insulates the plastic layer against the heat of explosion and helps to maintain structural integrity of the plastic layer after detonation of the explosive charge.

All components except the explosive charge and the innermost plastic layer and its associate stainless steel rim preferably constitute one sub-assembly. The remaining components make up a second sub-assembly which is attached to the helmet of the user.

Upon detonation of the explosive charges, the first sub-assembly is ejected to deflect the projectile.

The first sub-assembly has its outer rim designed to fit into the second sub-assembly outer rim. As previously mentioned, the second sub-assembly rim is designed to be attached to the user's helmet.

In use, when the face shield is met with an incoming projectile, the projectile may be deflected by the first layer. If penetration occurs at the first layer, the layer of glass beneath it is designed to shatter. The fracturing of the glass layer will break the copper wires which are embedded therein.

Breaking of the copper wires triggers the ignition by electrical means of the small explosive charges between the stainless steel rims.

As the projectile approaches the inner layers, the ignition of the explosive charge causes the outermost steel rim to push against the other plastic layer to accelerate the layer outwards towards the incoming projectile at a vector. The burn pattern of the explosive is designed to have the bottom charge detonated first and this allows the flame or burn of the charge to work its way up to the top charges. With the bottom portion of the face shield (the bottom portion of sub-assembly 1) going first, the top portion causes it to take a curved trajectory. When the top explosive charges detonate the steel rim, the plastic layer and the outer layer of glass are forced to move upwardly and away from the face. The first sub-assembly is thereby removed from the helmet. With the incoming projectile and the plastic layer colliding at vectors to each other, the collision will impart a deflection in the bullet away from its original course. It is possible that, even in the absence of deflection, the combined layers would be sufficient to absorb the impact of the incoming bullet or projectile without allowing penetration through the final layer.

After detonation of the explosive charges, a replacement first sub-assembly can be attached to replace the one that was launched.

The invention also contemplates a power source, which may be stored in the helmet itself, and an electronic controller which is activated by conventional means to detonate the explosive charges.

A suitable explosive charge may be generated by any suitable explosive material, such as gunpowder, black powder, or fast burning solid rocket fuels. The only requirements for the explosive charge is that the burn rate must be faster than the velocity of the incoming projectile to ensure launching of the shield before penetration.

It is preferable that the shield provide full facial protection by extending from the forehead area of the face down to the chin. An alternative embodiment would be a goggle-type shield which would only come down from the forehead to approximately the eye level of the user.

An optional metal or composite layer can be placed on top of the face shield to provide an extra degree of penetration protection as needed.

An object of the invention is to provide a face shield attachment apparatus to a helmet comprising, an outer layer made of glass material, a first inner layer made of high impact resistant plastic material, a first metal rim having an upper surface connected to peripheral edges of the plastic layer, an explosive charge disposed beneath an inner surface of the first metal rim, a second metal rim disposed beneath the explosive charge, a gaseous layer of inert material disposed between the outer glass layer and the inner plastic layer, trigger means, responsive to shattering of the outer glass layer, for igniting the explosive charge, wherein the outer glass layer, inner plastic layer, explosive charge, gaseous layer, trigger means and first and second metal rims comprise a first sub-assembly, a second inner layer made of high impact resistant plastic material, and a metal frame connected to peripheral edges of the second plastic layer, and providing means for connecting the second plastic layer to the helmet, wherein the second inner layer and the metal frame comprise a second sub-assembly, and wherein the rims of the first sub-assembly are received within the frame of the second sub-assembly.

Preferably, the trigger means comprises an inner layer of glass material having conductive, thin, closely spaced wires embedded therein, an igniter connected to the explosive charge, an electrical power source connected to the igniter, wherein breakage of the conductive wires triggers the power source to power the igniter and explode the charge.

The plastic layers are made of polycarbonate plastic or similar material.

The igniter initiates a controlled burn beginning at a bottom portion of the shield.

Preferably, the explosive charge is divided into upper and lower charges, and wherein the lower charges ignite before the upper charges.

An object is to provide a first sub-assembly which is launched from the second sub-assembly upon ignition of the explosive charge.

The metal rim, the frame and the glass and plastic layers are preferably held together with epoxy glue.

Another object of the invention is to provide a method of protecting facial areas of a user wearing an open-faced helmet comprising attaching a plastic inner shield to the helmet through a metal frame, attaching a multi-ply outer shield to the frame of the plastic inner shield through a metal rim, placing an explosive charge between the plastic inner shield and the multi-ply outer shield, triggering the explosive charge with trigger means operable by shattering an outer layer of the multi-ply outer shield, thereby launching the multi-ply outer shield at a vector to an incoming projectile, causing deflection of the projectile.

In the method, the trigger means comprises an inner layer of glass material having conductive, thin, closely spaced wires embedded therein, an igniter connected to the explosive charge, an electrical power source connected to the igniter, wherein breakage of the conductive wires triggers the power source to power the igniter and explode the charge.

BRIEF DESCRIPTION OF THE DRAWINGS

FIG. 6 is a cross-sectional view showing both sides of the assembly, with the drawing not to scale.

FIG. 7 is a detailed cross section of a variation of the embodiment of FIG. 6.

FIG. 7A is an enlarged cross section of a portion of FIG. 7.

FIG. 8 is an enlarged detail view of the outer rim sub-assembly.

DETAILED DESCRIPTION OF THE DRAWINGS

Figure 1:
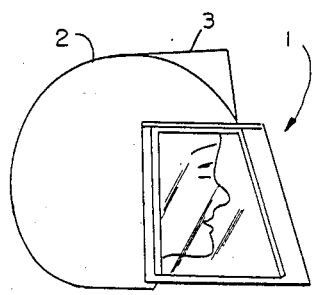
FIG. 1 is a side elevation of a preferred embodiment of the invention.

Referring to the drawings, FIG. 1 shows a shield generally referred by the numeral 1 which is attached to a helmet 2. An upper portion of the helmet 2 includes a power source and control unit 3 which powers and controls the explosive charges to be described later.

The shield 1 shown in FIG. 1 shows an inner shield and an outer shield which appear spaced apart. The outermost shield is of a multi-ply construction having as the outermost layer tempered glass. Tempered glass shatters in a particular manner suitable for the present invention.

Figure 2:
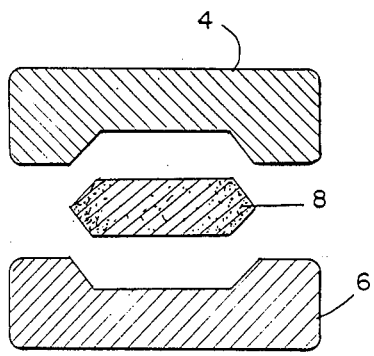
FIG. 2 is a cross-sectional view showing the two rims and an explosive charge disposed therebetween.
Figure 3:
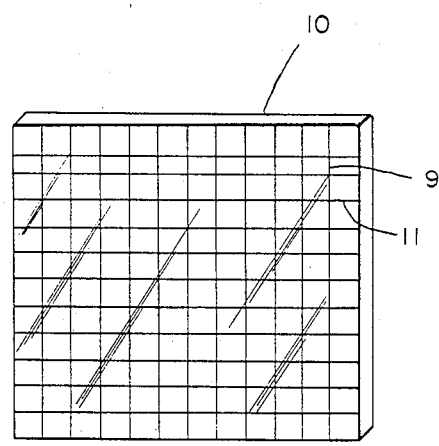
FIG. 3 is an enlarged view of the glass layer containing conductive wires.

The outer shield has an inner layer of plastic material which abuts along peripheral edges the upper surface of rim 4 shown in FIG. 2. Intermediate layers, between the inner plastic layer and the outer glass layer, include a layer of inert gas which prevents fogging of the shield. In the preferred embodiment, the second glass layer is provided next to the outer glass layer. The second glass layer is illustrated in FIG. 3 as numeral 10. Glass sheet 10 provides a trigger which facilitates ignition of the explosive charges 8 shown in FIG. 2. The explosive charges 8 are disposed between upper and lower rims 4, 6 which are preferably made of stainless steel. The stainless steel rims 4, 6 preserve the structural integrity of the previously described inner plastic layer of the outer shield.

The glass sheet 10 has conductive wires 9, 11 embedded therein which are thin enough to break when the glass layer 10 shatters. When the wire breaks, a signal is sent from the control unit to the power source to provide preferably electrically initiated ignition of the explosive charges. The explosive charge 8 shown in FIG. 2, upon explosion, would push apart the two rims 4, 6 and, since rim 4 would be connected to the inner plastic sheet of the outer shield, the rim and the inner plastic layer of the outer shield would be propelled outwardly away from the user's face.

Figure 4:
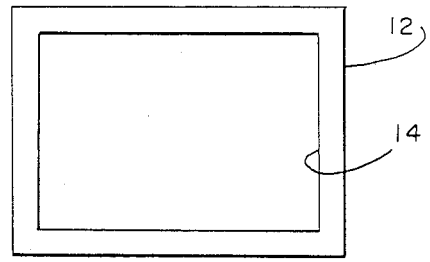
FIG. 4 is a plan view showing one of the rims.

In FIG. 4, a rim is shown to have outer edges 12 and inner edges 14. The rim shown in FIG. 4 can be either rim 4 or rim 6 since each is a substantial mirror image of the other.

Figure 5:
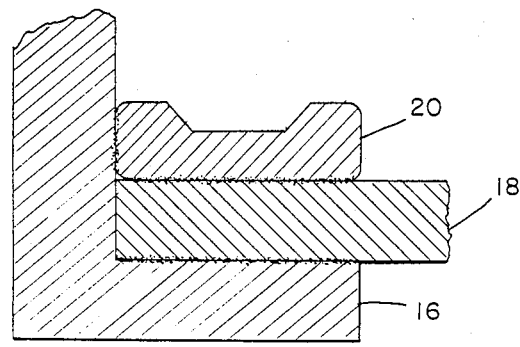
FIG. 5 is a detailed cross-sectional view showing the innermost shield.

From FIG. 5 it can be seen that frame 16, shown partly in section, which is attached to inner shield 18, also supports a rim 20 associated with the outer shield.

Inner shield 18 is another sheet of plastic material which is preferably thicker than the plastic layer used in the outer shield. Rim 20 and frame 16 protect the inner shield 18 from percussion associated with ignition of the explosive material.

FIG. 6 shows an assembly which depicts the face shield described above. An outer rim 22 is used to assemble an outer layer 24 of tempered glass, an inner layer 26 of glass with trigger wires embedded therein. A layer of inert gas 28 is provided between the inner glass layer 26 and a layer 30 of strong plastic material, such as polycarbonate. An innermost plastic layer 31 is provided closest to the user's face and is likewise made of a polycarbonate plastic. Elements 22, 24, 26, 28 and 30 form an outer rim subassembly 32 which is assembled with a second subassembly 34. Both the outer rim 22 and the inner rim 36 are made of stainless steel. Each rim has rim and frame portions as is apparent from the drawings.

As can be appreciated, the drawings of FIGS. 6-8 are not to scale and are shown with the component parts slightly separated for the purpose of illustration. Obviously, the actual assembly of subassemblies 32 and 34 would show a tight fit between the components without gaps.

Surface 38 of the rim 36 is used to attach the face shield to the helmet. Any suitable attachment means can be used, including adhesives of sufficient strength. It can also be appreciated that the overall shape of the shield can be adapted to the shape of the helmet such that the various layers may comprise curvilinear but parallel strate.

Explosive charges 40 are provided on opposite sides of the assembly and operate as described previously. A weather seal 42 may be provided between the two rim components to provide protection for the explosive charges from the elements.

It can also be appreciated that the trigger wires shown embedded in the layer 26 are shown without connection means for connecting the trigger to the explosive charge. However, this is within the purview of the practitioner in the art and ports may be provided in various portions of the assembly to provide a connection between the trigger wires and the explosive and/or a connection of the trigger wires to a fuse or other trigger means which is connected to the explosive charge such as fuse 43 connected to the trigger wires and power source 44 (shown schematically).

The embodiment of FIG. 7 is a slight variance on the FIG. 6 embodiment and is intended to show a composite frame structure. The layers are the same as the FIG. 6 embodiment and the rims operate in the same way.

FIG. 7 also shows that the plastic layer 30 is not as thick as the plastic layer 31. This is in keeping with the previous description in reference to the other drawings in which it is preferred that the innermost plastic layer 31 be stronger than the outermost plastic layer 30. This is to afford maximum protection for the user.

The composite frame structure of FIG. 7 includes the basic rims 22 and 36. However, instead of the rims being made of stainless steel entirely, the major portions of both rims 22 and 36 can be made of a lighter metal alloy or a strong plastic material so long as recessed portions are provided with stainless 23 and 25. The assembly of FIG. 7 with the composite structure is such that the frames are made of different material than the rims since the stainless steel areas 23 and 25 are provided in the rim portions while the frame portions are made of a different material. The stainless steel rims 23 and 25 are bonded to their respective frames by adhesive or by having the stainless steel rims molded into the frame material. As an example, FIG. 7A shows how a stainless steel portion 25 is embedded in the frame 36 whereby the frame 36 is molded around the stainless steel rim 25.

FIG. 8 shows a detail view of the outer rim 22. To hold the layers of glass and plastic in position, a small lip is incorporated into the rim. The lips 21 can be provided in the rim as needed in order to hold the various layers in position and separate from the inert gas layer 28. The lips 21 may be omitted if an adhesive of sufficient strength can serve the same purpose. A sealant 27 may be provided along the edges of the frame to keep the inert gas layer from escaping. The sealant 27 may be provided on any surfaces of the two subassemblies, particularly the first subassembly, to prevent escape of the inert gas.

While the invention has been described in reference to specific examples and embodiments, variations may be made without departing from the scope of the invention as embodied in the following claims.

I claim:

1. A face shield attachment apparatus to a helmet comprising,
   an outer layer made of glass material,
   a first inner layer made of high impact resistant plastic material,
   a first metal rim having an upper surface connected to peripheral edges of the plastic layer,
   an explosive charge disposed beneath an inner surface of the first metal rim,
   a second metal rim disposed beneath the explosive charge,
   a gaseous layer of inert material disposed between the outer glass layer and the inner plastic layer,
   trigger means, responsive to shattering of the outer glass layer, for igniting the explosive charge, wherein the outer glass layer, inner plastic layer, explosive charge, gaseous layer, trigger means and first and second metal rims comprise a first subassembly, a second inner layer made of high impact resistant plastic material, and a metal frame connected to peripheral edges of the second plastic layer, and providing means for connecting the second plastic layer to the helmet, wherein the second inner layer and the metal frame comprise a second sub-assembly, and wherein the rims of the first sub-assembly are received within the frame of the second sub-assembly.

2. The apparatus of claim 1 wherein the trigger means comprises an inner layer of glass material having conductive, thin, closely spaced wires embedded therein, an igniter connected to the explosive charge, an electrical power source connected to the igniter, wherein breakage of the conductive wires triggers the power source to power the igniter and explode the charge.

3. The apparatus of claim 1 wherein the plastic layers are made of polycarbonate plastic.

4. The apparatus of claim 3 wherein the igniter initiates a controlled burn beginning at a bottom portion of the shield.

5. The apparatus of claim 1 wherein the explosive charge is divided into upper and lower charges, and wherein the lower charges ignite before the upper charges.

6. The apparatus of claim 1 wherein the various layers form a slanted shield angling upwardly to deflect incoming projectiles.

7. The apparatus of claim 1 wherein the first sub-assembly is launched from the second sub-assembly upon ignition of the explosive charge.

8. The apparatus of claim 1 wherein the metal rim, the frame and the glass and plastic layers are held together with epoxy glue.

9. A method of protecting facial areas of a user wearing an open-faced helmet comprising, attaching a plastic inner shield to the helmet through a metal frame, attaching a multi-ply outer shield to the frame of the plastic inner shield through a metal rim, placing an explosive charge between the plastic inner shield and the multi-ply outer shield, triggering the explosive charge with trigger means operable by shattering an outer layer of the multi-ply outer shield, thereby launching the multi-ply outer shield at a vector to an incoming projectile, causing deflection of the projectile.

* * * * *